US00PP34785P2

(12) United States Plant Patent
Craigie et al.

(10) Patent No.: US PP34,785 P2
(45) Date of Patent: Nov. 29, 2022

(54) ***AGAPANTHUS* PLANT NAMED 'PMB020'**

(50) Latin Name: *Agapanthus orientalis*
Varietal Denomination: PMB020

(71) Applicant: PINE MOUNTAIN BOTANICS PTY. LTD., Pine Mountain (AU)

(72) Inventors: John Maxwell Craigie, Pine Mountain (AU); Gail Alexis Craigie, Pine Mountain (AU)

(73) Assignee: PINE MOUNTAIN BOTANICS PTY., LTD., Pine Mountain (AU)

( * ) Notice: Subject to any disclaimer, the term of this patent is extended or adjusted under 35 U.S.C. 154(b) by 0 days.

(21) Appl. No.: 17/590,460

(22) Filed: Feb. 1, 2022

(51) Int. Cl.
*A01H 5/02* (2018.01)
*A01H 6/04* (2018.01)

(52) U.S. Cl.
USPC ..... Plt./398
CPC ..... *A01H 6/04* (2018.05); *A01H 5/02* (2013.01)

(58) Field of Classification Search
USPC ..... Plt./398
See application file for complete search history.

*Primary Examiner* — Susan McCormick Ewoldt
(74) *Attorney, Agent, or Firm* — C. Anne Whealy

(57) ABSTRACT

A new and distinct cultivar of *Agapanthus* plant named 'PMB020', characterized by its upright plant habit, medium height; vigorous growth habit; numerous medium to large flowers with white-colored perianth segments; flowers arranged on dense and large inflorescences supported on upright and strong scapes; flowering annually in the late spring and early summer; and good garden performance.

3 Drawing Sheets

Figure 1:
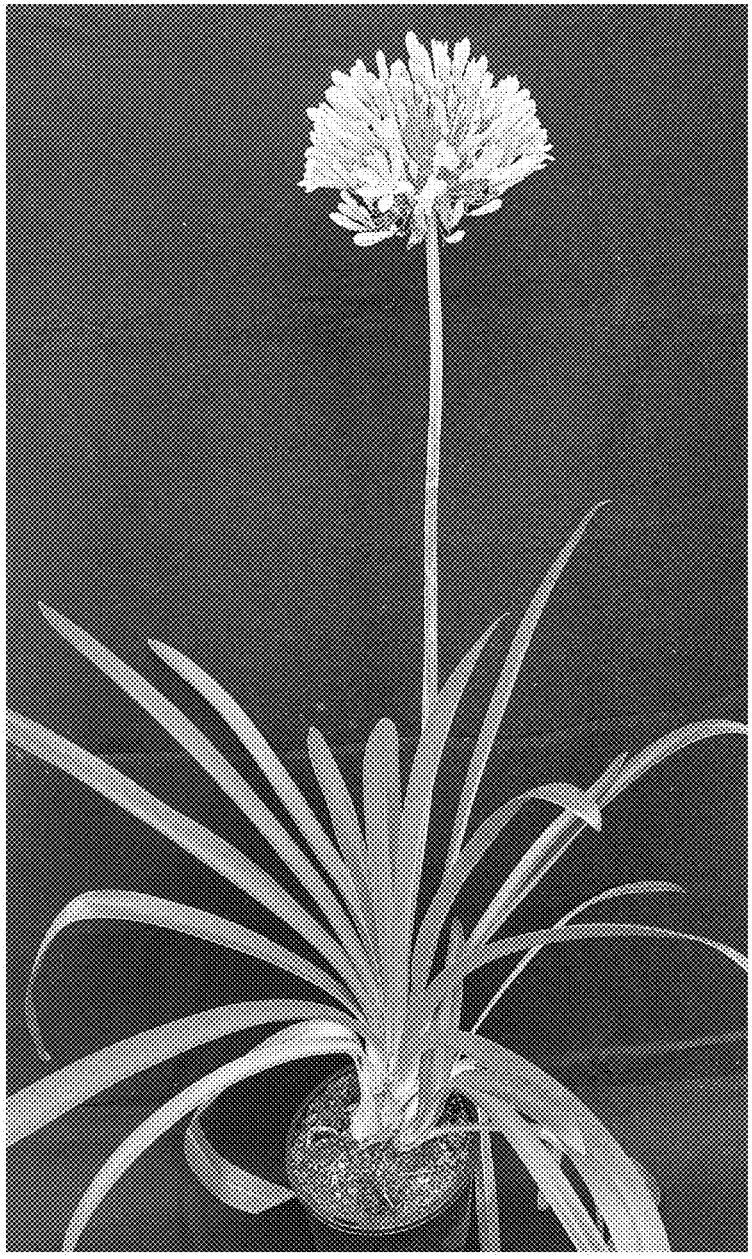

Botanical designation: *Agapanthus orientalis.*
Cultivar denomination: 'PMB020'.

CROSS-REFERENCED TO CLOSELY-RELATED APPLICATIONS

An Australian Plant Breeder's Rights application for the instant plant was filed by the Applicant/Assignee of the instant application, Pine Mountain Botanics Pty. Ltd. of Pine Mountain, Queensland, Australia on Apr. 9, 2020, application number 2020/063. Foreign priority is not claimed to this Australian Plant Breeder's Rights application.

BACKGROUND OF THE INVENTION

The present invention relates to a new and distinct cultivar of evergreen perennial *Agapanthus* plant, botanically known as *Agapanthus orientalis* and hereinafter referred to by the name 'PMB020'.

The new *Agapanthus* plant is the product of a planned breeding program conducted by the Inventors in Pine Mountain, Queensland, Australia. The objective of the breeding program is to create new vigorous and freely flowering *Agapanthus* plants with medium to large leaves, medium height and white-colored flowers on large inflorescences.

The new *Agapanthus* plant is the result of a cross-pollination made by the Inventors in 2008 of an unnamed selection of *Agapanthus orientalis*, not patented, as the female, or seed, parent with a proprietary selection of *Agapanthus orientalis* known as code designation aga09002, not patented, as the male, or pollen, parent. The new *Agapanthus* plant was discovered and selected by the Inventors as a single flowering plant from within the progeny of the stated cross-pollination in a controlled environment in Pine Mountain, Queensland, Australia in 2010.

Asexual reproduction of the new *Agapanthus* plant by divisions in a controlled environment in Pine Mountain, Queensland, Australia since 2011 has shown that the unique features of this new *Agapanthus* plant are stable and reproduced true to type in successive generations.

SUMMARY OF THE INVENTION

Plants of the new *Agapanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'PMB020'. These characteristics in combination distinguish 'PMB020' as a new and distinct *Agapanthus* plant:

1. Upright plant habit, medium in height.
2. Vigorous growth habit.
3. Numerous medium to large flowers with white-colored perianth segments.
4. Flowers arranged on dense and large inflorescences supported on upright and strong scapes.
5. Flowering annually in the late spring and early summer.
6. Good garden performance.

Plants of the new *Agapanthus* differ primarily from plants of the female parent selection primarily in inflorescence size as plants of the new *Agapanthus* have larger inflorescences than plants of the female parent selection.

Plants of the new *Agapanthus* differ primarily from plants of the male parent selection primarily in flower and inflorescence size as plants of the new *Agapanthus* have larger flowers and inflorescences than plants of the male parent selection.

Plants of the new *Agapanthus* can be compared to plants of *Agapanthus orientalis* 'WP003', disclosed in U.S. Plant Pat. No. 32,176. In side-by-side comparisons, plants of the new *Agapanthus* and 'WP003' differ in the following characteristics:

1. Plants of the new *Agapanthus* have longer and broader leaves than plants of 'WP003'.
2. Plants of the new *Agapanthus* flower later than and for a shorter period of time than plants of 'WP003'.
3. Plants of the new *Agapanthus* have larger flowers than plants of 'WP003'.
4. Plants of the new *Agapanthus* have larger inflorescences than plants of 'WP003'.
5. Plants of the new *Agapanthus* have taller and thicker scapes than plants of 'WP003'.

Plants of the new *Agapanthus* can be compared to plants of *Agapanthus orientalis* 'Snow Cloud', disclosed in U.S. Plant patent application Ser. No. 10/104,537 (now abandoned). In side-by-side comparisons, plants of the new *Agapanthus* and 'Snow Cloud' differ in the following characteristics:

1. Plants of the new *Agapanthus* have longer and broader leaves than plants of 'Snow Cloud'.
2. Plants of the new *Agapanthus* have smaller flowers than plants of 'Snow Cloud'.
3. Plants of the new *Agapanthus* have larger inflorescences with fewer flowers than plants of 'Snow Cloud'.
4. Plants of the new *Agapanthus* have shorter scapes than plants of 'Snow Cloud'.

Plants of the new *Agapanthus* can also be compared to plants of *Agapanthus orientalis* 'Andaval', also known as 'Great White', not patented. In side-by-side comparisons, plants of the new *Agapanthus* and 'Andaval' differ in the following characteristics:

1. Plants of the new *Agapanthus* have longer and narrower leaves than plants of 'Andaval'.
2. Plants of the new *Agapanthus* have slightly smaller flowers than plants of 'Andaval'.
3. Inflorescences of plants of the new *Agapanthus* are narrowly oblate in shape whereas inflorescences of plants of 'Andaval' are transverse elliptic in shape.
4. Plants of the new *Agapanthus* have longer scapes than plants of 'Andaval'.

BRIEF DESCRIPTION OF THE PHOTOGRAPHS

The accompanying colored photographs illustrate the overall appearance of the new *Agapanthus* plant showing the colors as true as it is reasonably possible to obtain in colored reproductions of this type. Colors in the photographs may differ slightly from the color values cited in the detailed botanical description which accurately describe the colors of the new *Agapanthus* plant.

The photograph on the first sheet (FIG. 1) is a side perspective view of a typical flowering plant of 'PMB020' grown in a container.

Figure 2:
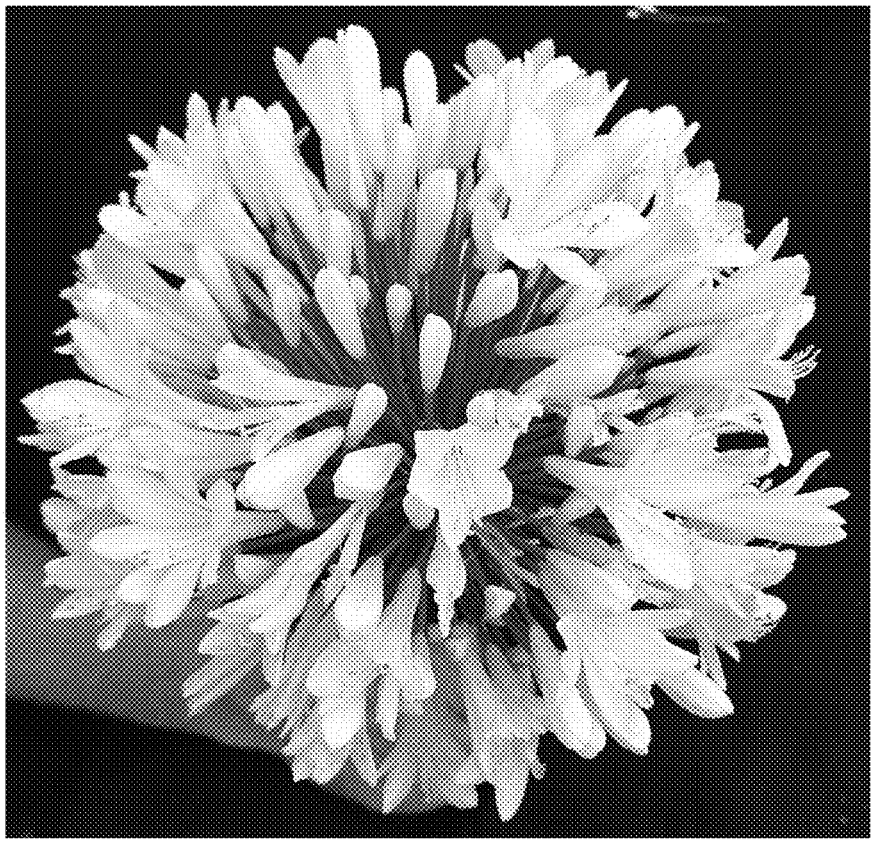

The photograph on the second sheet (FIG. 2) is a close-up view of a typical inflorescence of 'PMB020'.

Figure 3:
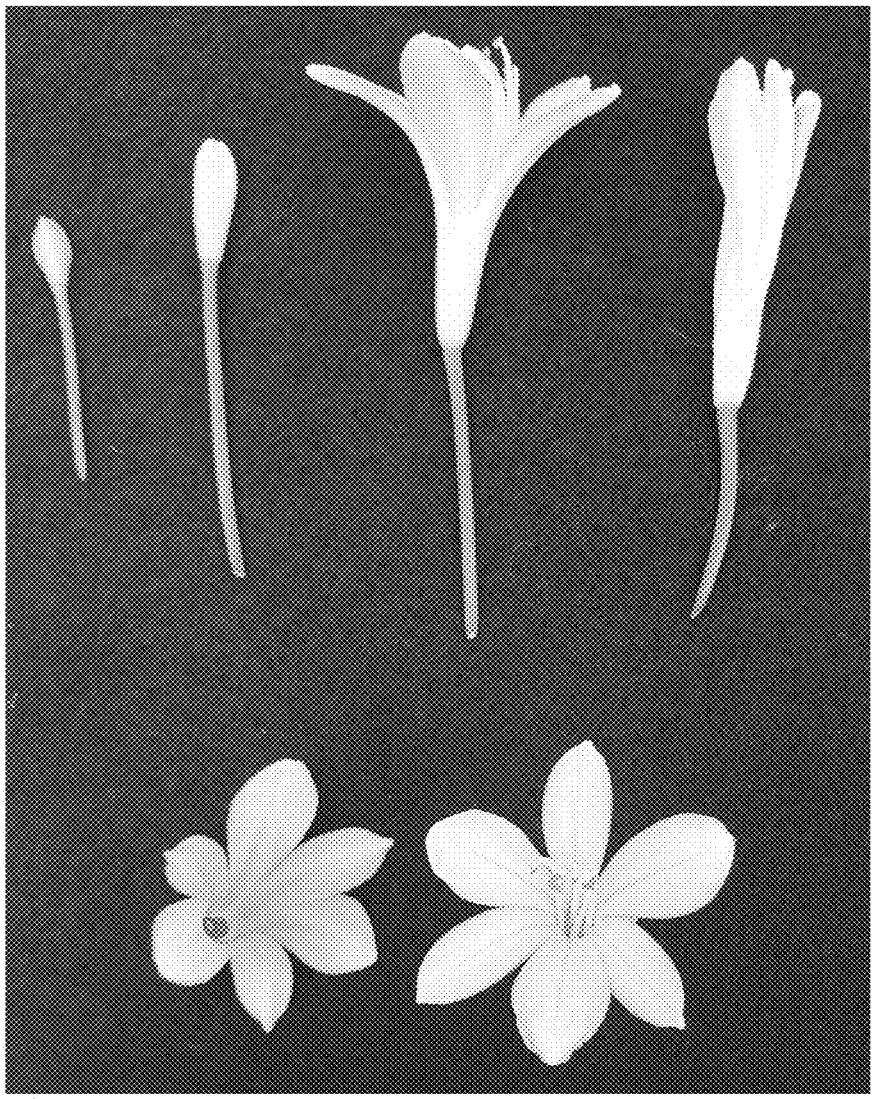

The photograph on the third sheet (FIG. 3) are close-up views of typical developing flower buds and flowers of 'PMB020'.

DETAILED BOTANICAL DESCRIPTION

The aforementioned photographs and following observations, measurements and values describe plants grown during the early summer (November) in 20-cm containers in a outdoor nursery in Pine Mountain, Queensland, Australia and under cultural practices typical of commercial *Agapanthus* production. Plants were one year old when the photographs and description were taken. In the following description, color references are made to The Royal Horticultural Society Colour Chart, 2015 Edition, except where general terms of ordinary dictionary significance are used.

Botanical classification: *Agapanthus orientalis* 'PMB020'.

Parentage:

*Female, or seed, parent*.—Unnamed selection of *Agapanthus orientalis*, not patented.

*Male, or pollen, parent*.—Proprietary selection of *Agapanthus orientalis* identified as code number aga09002, not patented.

Propagation:

*Type*.—By in vitro meristem culture.

*Time to initiate roots, summer*.—About seven to ten days at substrate temperatures ranging from 18° C. to about 20° C. and ambient temperatures ranging from 28° C. to about 35° C.

*Time to initiate roots, winter*.—About 18 to 21 days at substrate temperatures ranging from 8° C. to about 12° C. and ambient temperatures ranging from 18° C. to about 25° C.

*Time to produce a rooted young plant, summer*.—About 28 to 35 days at substrate temperatures ranging from 18° C. to about 20° C. and ambient temperatures ranging from 28° C. to about 35° C.

*Time to produce a rooted young plant, winter*.—About 56 to 62 days at substrate temperatures ranging from 8° C. to about 12° C. and ambient temperatures ranging from 18° C. to about 25° C.

*Root description*.—Thick and fleshy; white in color.

*Rooting habit*.—Moderately freely branching; medium density.

Plant description:

*Plant form and growth habit*.—Evergreen flowering perennial plant; upright plant habit, medium in height and strong upright flower scapes; leaves and flowering stems basal; vigorous growth habit.

*Plant height, soil level to top of foliar plane*.—About 55 cm to 60 cm.

*Plant height, soil level to top of floral plane*.—About 90 cm.

*Plant width* (*spread*).—About 60 cm to 70 cm.

Leaf description:

*Arrangement and appearance*.—Strap-like leaves arranged in a basal rosette with about 18 leaves developing per plant; leaves distichous, simple and sessile; leaves erect to semi-erect in attitude and outwardly arching with development.

*Leaf length*.—About 60 cm.

*Leaf width*.—About 3.9 cm.

*Shape*.—Ligulate; slightly recurved.

*Apex*.—Broadly acute.

*Margin*.—Entire.

*Texture and luster, upper and lower surfaces*.—Smooth, glabrous; slightly glossy and slightly glaucous.

*Venation pattern*.—Parallel.

*Color*.—Developing leaves, upper and lower surfaces: Close to 146B. Fully expanded leaves, upper and lower surfaces: Close to 146B to 146C; venation, close to 146B to 146C.

Flower description:

*Flower type and flowering habit*.—Single funnel-shaped flowers arranged in terminal umbels supported by strong upright scapes; flowers medium to large in size; flowers face upright to outwardly depending on position on the umbel; umbels large and narrowly oblate in shape; freely flowering habit with about 246 flowers developing per umbel.

*Fragrance*.—None detected.

*Natural flowering season*.—Mid-season flowering habit; under natural conditions, plants of the new *Agapanthus* being flowering during the middle to late spring in southeastern Queensland, Australia.

*Postproduction longevity*.—Flowers last about three to four weeks on the plant; flowers not persistent.

*Flower buds*.—Length: About 1.8 cm. Diameter: About 6 mm to 7 mm. Texture: Smooth, glabrous. Color: Close to 155B.

*Inflorescence diameter*.—About 20 cm.

*Flower diameter*.—About 3.9 cm.

*Flower tube length*.—About 1.7 cm.

*Perianth*.—Quantity and arrangement: Typically six to seven segments arranged in a single whorl; lower part of a segment is fused into a narrow tube; upper part of a segment is free and flaring outwardly. Segment length: About 2.7 cm. Segment width: About 1.2 cm. Segment lobe shape: Obovate. Segment apex: Acute to acuminate. Segment margin: Entire; slightly undulate. Segment texture, upper and lower surfaces: Smooth, glabrous. Segment color, mature flower: Inner and outer surfaces: Close to NN155D; venation, close to NN155D. Tube and throat: Close to NN155D; venation, close to NN155D.

*Peduncles* (*scapes*).—Length: About 80 cm. Diameter: At mid-section, about 1.3 cm. Strength: Strong. Aspect: Mostly upright. Texture: Smooth, glabrous. Color: Close to 147B.

*Pedicels*.—Length: About 5.1 cm. Diameter: About 1.8 mm. Aspect: Upright to horizontal from the peduncle axis. Strength: Strong. Texture: Smooth, glabrous. Color: Close to 146B.

*Reproductive organs*.—Stamens: Quantity per flower: Typically six. Filament length: About 3 cm. Filament color: Close to NN155D. Anther shape: Oblong; dorsifixed. Anther length: About 1 mm to 1.5 mm. Anther color: Close to 163B. Pollen color: Close to 163B. Pistils: Quantity per flower: One. Style length: About 3 cm. Style color: Close to NN155D. Stigma shape: Clavate. Stigma color: Close to NN155D.

*Fruits*.—Type: Three-sided capsule. Length: About 2.5 cm to 3.5 cm. Diameter: About 9 mm to 11 mm. Color: Close to 144A to 144B.

*Seeds*.—Quantity per fruit: Typically about seven to twelve. Length: About 9 mm to 12 mm. Diameter: About 3 mm. Texture: Smooth, glabrous. Color: Close to 202A.

Pathogen & pest resistance: To date, plants of the new *Agapanthus* have not been noted to be resistant to pathogens and pests common to *Agapanthus* plants.

Garden performance: Plants of the new *Agapanthus* have been observed to have good garden performance and to tolerate drought and temperatures ranging from −3° C. to about 38° C.

It is claimed:

1. A new and distinct *Agapanthus* plant named 'PMB020' as illustrated and described.

* * * * *